United States Patent
Prins et al.

(10) Patent No.: US 9,237,879 B2
(45) Date of Patent: Jan. 19, 2016

(54) METHOD OF MANUFACTURING AN ULTRASOUND TRANSDUCER AND DEVICES INCLUDING AN ULTRASOUND TRANSDUCER

(71) Applicant: Oldelft B.V., Delft (NL)

(72) Inventors: Christian Prins, Delft (NL); Jacob Alexander Ponte, Delft (NL); Zili Yu, Delft (NL)

(73) Assignee: OLDELFT B.V., Delft (NL)

( * ) Notice: Subject to any disclaimer, the term of this patent is extended or adjusted under 35 U.S.C. 154(b) by 215 days.

(21) Appl. No.: 13/790,480

(22) Filed: Mar. 8, 2013

(65) Prior Publication Data

US 2013/0245450 A1    Sep. 19, 2013

(30) Foreign Application Priority Data

Mar. 9, 2012 (NL) .................................. 2008459

(51) Int. Cl.

| | |
|---|---|
| H04R 31/00 | (2006.01) |
| A61B 8/00 | (2006.01) |
| B06B 1/06 | (2006.01) |
| H01L 41/338 | (2013.01) |
| H01L 21/768 | (2006.01) |
| A61B 8/12 | (2006.01) |
| H01L 41/18 | (2006.01) |

(52) U.S. Cl.
CPC ............. *A61B 8/4444* (2013.01); *A61B 8/12* (2013.01); *A61B 8/4477* (2013.01); *A61B 8/4494* (2013.01); *B06B 1/0622* (2013.01); *H01L 21/76879* (2013.01); *H01L 41/183* (2013.01); *H01L 41/338* (2013.01); *A61B 8/445* (2013.01)

(58) Field of Classification Search
None
See application file for complete search history.

(56) References Cited

U.S. PATENT DOCUMENTS

| | | | | |
|---|---|---|---|---|
| 5,834,687 | A * | 11/1998 | Talbot et al. | 174/386 |
| 6,759,740 | B2 * | 7/2004 | Onitani et al. | 257/705 |
| 2005/0094490 | A1 | 5/2005 | Thomenius et al. | |
| 2006/0028099 | A1 * | 2/2006 | Frey | 310/334 |
| 2009/0034370 | A1 * | 2/2009 | Guo | 367/180 |
| 2009/0069686 | A1 | 3/2009 | Daft et al. | |
| 2010/0168581 | A1 * | 7/2010 | Knowles et al. | 600/459 |

FOREIGN PATENT DOCUMENTS

WO    WO 2007017776 A2    2/2007

OTHER PUBLICATIONS

International Search Report from European Patent Office for NL 2008459 dated Oct. 17, 2012.

* cited by examiner

*Primary Examiner* — Reema Patel
(74) *Attorney, Agent, or Firm* — Shumaker, Loop & Kendrick LLP

(57) ABSTRACT

A method of manufacturing an ultrasound transducer for an ultrasound imaging device including a plurality of transducer elements arranged in a two dimensional array on a single carrier of semi-conductor material including the step of providing a buffer layer between the carrier and a layer including piezo electrical material, the buffer layer having a thickness arranged for dicing each of the plurality of transducer elements on the carrier.

12 Claims, 4 Drawing Sheets

METHOD OF MANUFACTURING AN ULTRASOUND TRANSDUCER AND DEVICES INCLUDING AN ULTRASOUND TRANSDUCER

CROSS-REFERENCE TO RELATED APPLICATION

This application claims priority to Dutch Patent Application No. 2008459 filed Mar. 9, 2012, the contents of which are incorporated by reference herein.

TECHNICAL FIELD AND BACKGROUND OF THE INVENTION

The present invention relates to a method of manufacturing an ultrasound transducer for use in an ultrasound imaging device. The present invention further relates to an ultrasound transducer manufactured according to the method. The present invention further relates to an ultrasound probe including at least one ultrasound transducer manufactured according to the method.

Ultrasound transducers are, for example, applied in ultrasound imaging devices. Herewith, images can be made of, for example, the heart of a human or animal. As the esophagus is close to the heart, often trans-esophageal echos (TEE) are made with such ultrasound transducers to visualize the heart. The TEE probes including the ultrasound transducers are arranged to generate images with a resolution corresponding to the aperture of the beam, the used frequency and the amount of transducer elements on the tip of the probe, among others. Other applications for such ultrasound transducers are also known, for example, to be applied in a blood vessel, heart chamber, or body cavity such as the vagina, rectum or nose to examine organs such as the uterus, prostate, stomach and so on.

Ultrasound imaging devices include, as described above, an ultrasound probe including the transducer having a plurality of individual transducer elements. Further, they include a central processing unit that controls the probe and renders the images from the acoustic signals derived from the probe. The central processing unit, in the form of a computer, can further be connected with a display to display the images, a keyboard or other input device to control the computer, and often storage devices to store the images thereon.

The probe forms an important part of the ultrasound imaging device, as it contains the transducer elements that transmit and receive ultrasound energy towards and from the target area, for example, the heart. Probes are found in different shapes and sizes, depending upon the application. Large probes can include a greater number of transducer elements and electronic circuitry, which has a positive effect on the resolution of the image. However, when larger probes are used internally, they are uncomfortable and allow less freedom of movement. With regard to the esophagus of a child, it is sometimes impossible to use a large probe at all.

It is known to arrange the transducer elements in a one dimensional array to generate a two dimensional image. One dimensional arrays can be steered, rotated or translated by the operator. These movements of the probe, however, can be very uncomfortable for the patient when used internally.

State of the art ultrasound transducers include a plurality of transducer elements arranged in a two dimensional array to generate a three dimensional image. Even four dimensional images are known, wherein plural images generated from a two dimensional array are combined over time, giving a real time, or near real time, three dimensional image.

Disadvantageously, two dimensional array ultrasound transducers are complex. They include, for example, a carrier layer having a two dimensional array of conductive pads and a plurality of piezo electric elements thereon. With the piezo electric elements, mechanical stress (vibration) is converted to and from an electrical potential. The piezo electric elements are on one side electrically connected with an individual conductive pad, and on the other side electrically connected with the other piezo elements and grounded, typically by applying a grounding layer over the plurality of individual piezo elements. As these transducer elements are arranged in a two dimensional array, the amount of transducer elements is very large, especially if a certain image resolution is required. For example, a relative small array of 32×32 includes 1,024 transducer elements. Each transducer element is connected individually, as the electrical signals transmitted or received therewith/therefrom are provided or read for further processing. Manufacturing these arrays is thus challenging.

Optimum transducer performance requires an optimum acoustic isolation of the array between each individual element. A gap between the elements filled with air may provide such an acoustic isolation. These gaps, however, increase the structural dimensions of the array and make the individual elements less stable as the physical strength of the array is lowered because of the gaps. The process of dicing the individual transducer elements from the array is also a delicate step in the manufacturing of the ultrasound transducer.

Furthermore, as each transducer element needs to be connected individually for applying an electrical signal or to read-out the electrical signal, connecting the transducer elements is challenging. Connecting each individual transducer element for further processing outside the probe would require a cable bundle with a huge amount of wires. This would not be practical because a cable with a large number of wired would be too large and inflexible to be provided through the esophagus or other body cavities. Therefore, at least some electric circuitry is needed in the probe to drive a group of individual transducer elements and lower the amount of wires needed. Electric circuits, however, increase the dimensions of the probe and complicate its construction.

Accordingly, there is a need for an ultrasound transducer that provides a high resolution image using an array of transducer elements, wherein the probe is smaller and less complex than conventional transducers.

BRIEF SUMMARY OF THE INVENTION

It is an object of the present invention to provide a method for manufacturing an ultrasound transducer, and an ultrasound transducer manufactured according to the method that overcomes the disadvantages of the prior art.

It is a further object of the present invention to provide a method for manufacturing an ultrasound transducer having limited dimensions without lowering the imaging resolution.

In a first aspect, provided herein is a method of manufacturing an ultrasound transducer for use in an ultrasound imaging device including a plurality of transducer elements arranged in a two dimensional array on a single carrier of semi-conductor material, the ultrasound transducer comprising a stack of layers, and the method including the steps of: providing a carrier of semi-conductor material including a two dimensional array of conductive pads, the carrier of semi-conductor material including electronic circuitry connected with the conductive pads for further processing outside the ultrasound transducer; providing on the carrier a layer including piezo electrical material covering the two dimensional array of conductive pads; separating each of the plurality of transducer elements by dicing the two dimensional array on the carrier; providing a grounding layer on the plurality of transducer elements for grounding each transducer element; and providing a buffer layer between the carrier and the layer including the piezo electrical material. The buffer layer has a thickness that it is arranged for dicing each of the plurality of transducer elements on the carrier.

Esophagus probes can include a single transducer, wherein the transducer elements thereof transmit and receive ultrasound energy. In another example, these ultrasound probes include two ultrasound transducers, wherein the transducer elements of one transducer are arranged for transmitting ultrasound, and the transducer elements of the other for receiving ultrasound. In order to cover a three dimensional, 3D plane, two dimensional, 2D grid, an array of individual transducer elements are provided. In order to generate an image, 3D or four dimensional, 4D, with a certain minimum resolution, a large amount of transducer elements is required. Arrays comprising over 2000 individual transducer elements are common.

To reduce the amount of wires to connect each of these 2000 and above individual transducer elements, electronic circuitry is provided to combine at least some individual transducer element so they can use a single wire. Solutions for electronic circuitry for multiplexing and transmitting a plurality of electronic signals over a single wire are known. Electronic circuitry to multiplex the electronic signals can be provided in a wafer die, wherein these circuits are present in the semiconductor layers of the wafer die. The wafer die includes on a top side a plurality of conductive pads, one pad for each transducer element. On the lower side, the wafer die is arranged for further processing the multiplex electronic signals, in most cases also in the form of a plurality of conductive pads. In the case of, for example, an ultrasound transducer having a 30×30 array of 900 individual transducer elements, and electronic multiplexing circuitry in the wafer die arranged to multiplex 9 signals (of a 3×3 sub-array), the wafer die includes on the top side 900 conductive pads and 100 bond pads. These bond pads can, for example, be connected by bond wires for further processing outside of the probe.

For a working ultrasound transducer, at least transducer elements, such as piezo elements, are provided on the conductive pads of the wafer die. These transducer elements are arranged to convert electrical energy from material stress to electrical energy and vice-versa. To close the individual electric circuit including a single conductive pad and a piezo element, these piezo elements are connected to ground.

Applying 900 individual piezo elements on the 900 conductive pads is physically challenging. However, there are alternative manufacturing methods. When even more piezo elements are used, examples of above 2000 elements (45×45 arrays) are common, there is an increasing need for these alternatives. Therein, the wafer die including the 900 conductive pads is provided first, then, in a simplified construction, a layer of piezo electrical material is applied on top thereof. From this layer of piezo electric material, individual piezo electric elements are formed by a dicing step. Therein, only the piezo electric material including layer is diced, not the wafer die below, acting as a carrier layer for the piezo layer. Subsequently, as a result of the dicing, a single wafer carrier die with electronic circuitry for multiplexing and including a plurality of conductive pads is formed having a plurality of individual piezo electric elements. The amount of conductive pads corresponds with the amount of piezo electric elements. Finally, on the whole wafer die, on top of the piezo elements, a grounding layer is provided to connect each piezo electric element with ground and close the electric circuit.

Dicing the individual piezo elements out of the layer of piezo electric material without damaging the electronic circuitry in the wafer carrier die is a major challenge that needs to be performed at an extreme level of precision. If the dice/cut is not deep enough, the piezo elements are not separated and a short circuit between two individual piezo circuits occurs, causing errors in the signal processing for the image generation. If the cut is too deep, the electronic circuitry below the surface of the wafer carrier die is damaged, causing errors in multiplexing the electronic signals from the individual piezo circuits, also resulting in errors in the signal processing for the image generation.

According to a first aspect of the invention, a method for manufacturing an ultrasound transducer for an ultrasound imaging device includes the step of providing an additional layer on the wafer carrier. This additional layer, acting as a buffer layer for dicing, is provided between the wafer carrier and the layer of piezo elements. In a further aspect, there can even be intermediate layers between the buffer layer and the wafer carrier and between the buffer layer and the layer of piezo elements, for example to increase the acoustic properties of the stack.

With the buffer layer, an additional thickness is created to simplify the dicing of the individual piezo elements. The thickness of the layer is related to the preciseness of the dicing in that the thicker the buffer layer, the more tolerance allowed in the depth of dicing the piezo electrical material layer.

According to a further aspect, a mask is applied to the buffer layer in a pattern that corresponds with the two dimensional array of conductive pads. Then, the buffer layer is etched, thereby removing parts of the layer according to the pattern. As a result thereof, holes are provided in the buffer layer in which the conductive pads of the carrier below are exposed. These holes, or buckets, have a depth similar to the thickness of the buffer layer. Therefore, the buffer layer is present in the form of a grid (or a grid of buckets) wherein all material is removed at the location of the conductive pads. The conductive pads are exposed at the bottom of the buckets. The piezo electric material layer is provided on top, and is subsequently diced by cutting the stack from the top side until the buffer layer is reached. A workable tolerance for cutting is herewith provided, which tolerance corresponds with the thickness of the buffer layer.

By applying the mask and subsequently etching the buffer layer, the material from which the buffer layer is constructed is removed from the individual piezo circuits as the piezo elements are electronically connected with the conductive pads without the buffer layer as an intermediate layer. However, at those positions on the stack where no piezo elements/conductive pads are arranged, the material of the buffer layer is still present. These positions correspond with the positions where cuts are applied during the step of dicing. The buffer layer is thus present in the form of a grid.

For the dicing step, dicing techniques such as laser cutting are applicable. The buffer layer, or at least those parts of the buffer layer that remain after etching, enable a dicing tolerance (buffer) corresponding to the thickness of the buffer layer. The buffer parts remaining in the buffer layer do not form part of the electronic circuitry of the individual piezo stacks. The electric signals from the piezo stack are not distorted by the buffer layer itself.

The material of the buffer layer is chosen based on its ability to form a thick layer. Such materials can have acoustic properties that do not match with the acoustic properties of the adjacent layers, and therefore reflect the acoustic signals to a certain height. The material contained in the buffer layer is thereof chosen by its ability to be applied in thick layer with a high level of acoustic transparency.

In another aspect, the method further includes the step of providing a layer including electrically conductive material on the buffer layer for electrically connecting the layer of piezo electric material with the conductive pads in the buckets of the carrier.

Upon processing the buffer layer between the piezo electric layer and the carrier by the steps of masking and etching, buckets are formed. At the bottom of each bucket lies a conductive pad. The wall of the bucket is formed by the buffer layer. Therefore, the height of the wall corresponds with the thickness of the buffer layer. A certain thickness is needed to be able to dice the piezo elements with a certain tolerance. By applying an additional layer including electrical conductive material on the buffer layer, the contact surface of the conductive pads can be increased, for at least the walls of each bucket. Further, the additional layer of conductive material can also be provided at at least a part of the top of the buffer layer, in between the buckets. Herewith, the contact surface of the conductive pads is increased further with parts outside of the bucket.

If in the latter case, the top of the buffer layer is contained with the additional layer of electrically conductive material, all contact pads can be electrically connected with each other. However, upon the dicing step, these connections are cut, separating each piezo element.

The material for the additional layer is chosen based on it's electrical conductivity and processing ability. And, because of its minimal thickness, for example approximately 4 µm, the layer is acoustically transparent. In a preferred embodiment, the layer has a minimal thickness and includes material that is easy applied to the wafer stack/carrier layer, and has a high level of electrical conductivity.

In yet another aspect, the method includes the step of providing a layer including electrically conductive filler for filling the buckets including the conductive pads. In a specific example, the filler is glue which is more or less in a fluent form upon applying the layer, and therefore arranged to fill each bucket.

As the electrically conductive filler or glue fills the bucket, it forms part of the piezo stack/piezo circuitry. The specific material therefore is arranged to acoustically match the adjacent layer, respectively the carrier or electric conductive layer on the carrier and the piezo electric layer. The material is optimized to match in acoustic impedance corresponding to the frequencies upon which the piezo elements operate.

In a further aspect, there can be additional layers to acoustically match adjacent layers. For example, in between the layer including the piezo electric material and the grounding layer, such an acoustic layer can be provided to match the acoustic impedance of the adjacent layers, or with the environment in which the transducer is to be operated, or the target to be sampled.

In a further aspect, the buffer layer includes an electric isolating material, and in another specific aspect, it comprises aluminium oxide. In yet another example, the buffer layer material has acoustically transparent properties. The buffer layer material fulfils certain requirements, such as having an acoustical impedance, and that it is acoustically transparent for the ultrasound waves at such a thickness that it is arranged for a workable tolerance at dicing the piezo elements. Furthermore, it is electrically isolating to prevent short-circuits between individual piezo elements. In one example, aluminium oxide fulfils at least some of these requirements.

In another aspect, the step of separating each of the plurality of transducer elements by dicing the acoustic stack according to the two dimensional carrier is performed by a step of scribing, breaking, sawing, laser cutting or the like. The most suitable method of dicing can be selected accordingly.

In a further aspect, the electronic circuitry in the wafer carrier is arranged to aggregate plural transducer elements for further processing outside of the ultrasound transducer over a reduced amount of wires. To overcome the problem of processing a large amount of electronic signals for the plurality of transducer elements, several solutions are known. For example, a method is provided to apply fibre optics as the communication medium. Fibre optics are arranged to transmit a larger bandwidth, increasing the amount of data to be transferred over the medium. Including fibre optics in transducer probes, however, requires converting electronic signals provided from the transducer/piezo elements into optical data. Digital optical modulators are thus required to be incorporated into the probe, while negatively impact the dimensions of the probe. Furthermore, the optical modulator circuitry can produce crossover on the signals.

In another aspect, multiplexing electronic circuitry is provided in the wafer carrier, which is arranged to multiplex electronic signals provided by each of the individual transducer elements (piezo circuitry) into a single signal arranged to be transmitter over a single wire, for example, a coaxial cable. In another aspect, frequency division multiplexing circuitry can be arranged in the wafer carrier or below the wafer carrier to combine plural electronic signals. Each signal is assigned to a different frequency within a specific frequency domain, thereby optimizing the available bandwidth of the coaxial cable. Other types of multiplexing electronic circuitry are also usable, depending on the further requirements. Other multiplexers can be used such as time division multiplexers or code division multiplexers.

In a further aspect, an ultrasound transducer is provided, including a stack of layers, manufactured by one or more of the aspects described above.

In a further aspect, an ultrasound probe is provided, including at least one ultrasound transducer produced by the method according to any one or more of the aspects described above.

DETAILED DESCRIPTION OF THE INVENTION

Figure 1:
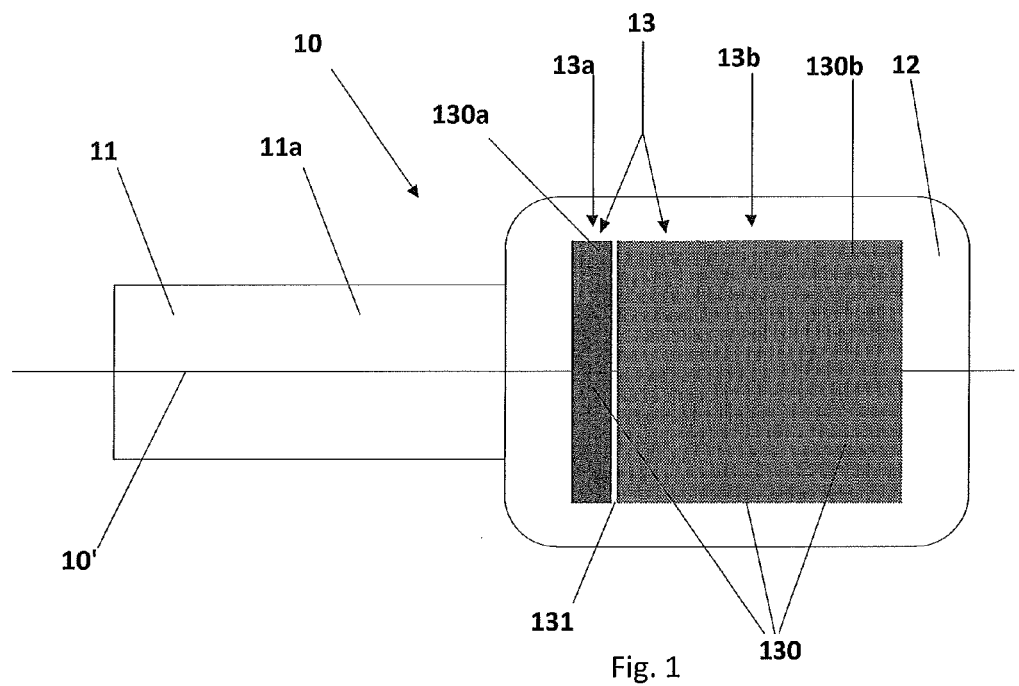
FIG. 1 illustrates an example of an ultrasound imaging device comprising a transducer manufactured according to an embodiment of the invention.

Like parts are shown with the same reference numerals.

FIG. 1 illustrates an example of an ultrasound imaging device including an ultrasound transducer manufactured according to an aspect of the invention. At reference numeral 10, an ultrasound imaging device is shown in the form of a probe, such as a probe is to be inserted in a body cavity, such as a trans-nasal or trans-oesophageal probe. The ultrasound probe 10 is provided with a shaft 11 extending along a longitudinal axis 10'. The shaft 11 has at its end 11a a gastroscope head or tip 12 in which an ultrasound transducer 13 is accommodated.

The ultrasound probe 10 includes a tubular member or gastroscope 11-12 for insertion in a body cavity of a patient's body, such as through the mouth and down the esophagus towards the region of the heart. This kind of transducer instrument is provided with a multi-element 2D array ultrasound transducer 13 and can therefor generate a three-dimensional (3D) image or a real time four-dimensional (4D) image of the target area such as the heart.

The transducer 13 typically includes a matrix of 1000+ piezo elements 130 comprised of a piezo electric, or "piezoelectric", material such as a ceramic. The piezo elements 130 are individually addressed to transmit and receive acoustic energy. As the tubular member or shaft 11 of a gastroscope is to be inserted through the mouth and down the oesophageal, its construction is flexible and limited in dimensional diameter. The cable thus contains a limited amount of wires for connection of the transducer, as more wires would decrease the flexibility and increase the diameter.

Due to the limited available space within the patient's body, the tip 12 of the probe 10 of the gastroscope has a construction of limited dimension and the dissipated power is as low as possible. Interconnecting 1000+ (or even 2000+) piezo elements 130 to their respective electronic circuitry within the tip 12 and/or shaft 11, as well as the multitude of high-voltage transmit signals and low-voltage receive signals, which are to be fed through the shaft 11 outside the patient's body towards the 3D image generating and processing equipment, imposes a technological challenge.

The ultrasound transducer shown in FIG. 1 includes two 2D-arrays, which can be used in an application wherein the high voltage driver circuitry is separated from the low voltage receipt circuitry. Depending upon the beam generating driver circuitry in or below the wafer carrier, but in particular upon the type of piezo electric material in the piezo layer and the thickness of the layer, the transducer element can be used for superharmonic imaging wherein second, third, fourth or even higher harmonics of a nonlinear received signal are combined. Higher harmonics increase the 'resolution' of the image. In a more practical embodiment, a 3 MHz transmit signal is applied for transmitting acoustic energy, and a second harmonic 6 MHz signal is received. Transducer array bandwidth, however, limits the processing of higher harmonics, third, fourth and higher harmonics require higher bandwidth than the transducer array can handle. Variations in operating frequencies of the individual transducers and use of smart array patterns can make processing of third and higher harmonics possible.

Figure 2:
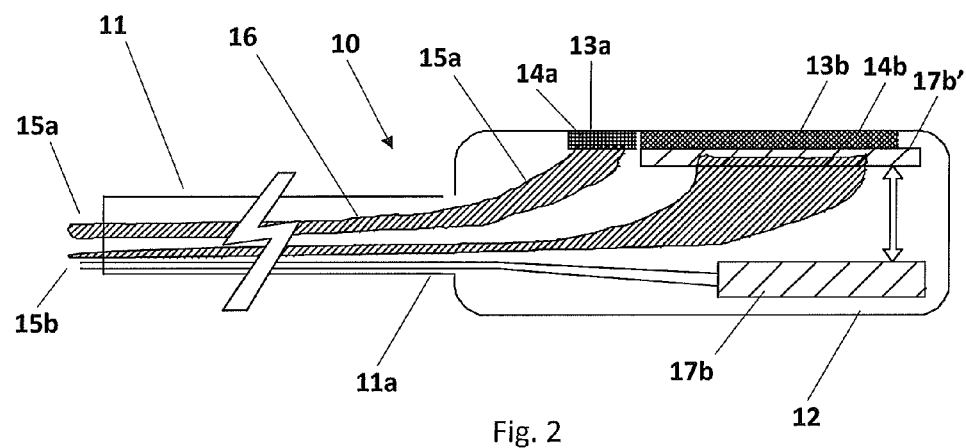
FIG. 2 illustrates a cross section of the ultrasound imaging device of FIG. 1.

As depicted in FIGS. 1 and 2, a dual ultrasound transducer, being a transducer comprising two 13a, 13b 2D transducer arrays is shown. A first 2D transducer array 13a is used to emit acoustic energy towards a target location within the patient's body. The transducer elements 130 of this first array 13a are optimized to emit acoustic energy using a high-voltage excitation circuitry located in either the image generating and processing equipment, or in the probe itself (not shown), for example in the wafer carrier, and are fed (or energized) via transmit signal line 15a.

The dual ultrasound transducer 13 also includes a second array 13b of transducer elements 130b, which second array 13b is capable of receiving the acoustic energy being reflected from the target location. In tip 12, suitable low-energy reception circuitry is accommodated which converts the acoustic energy as electrical signals to the low-voltage reception electronics 17b that combines them into a lower number of signals that are transmitted via output signal lines 15b to suitable image generating and processing equipment (not shown).

One 2D-array (first array 13a) is dedicated to the transmission of ultrasound energy, while the other 2D-array (second array 13b) is dedicated to the reception of ultrasound energy. The transmit array 13a and corresponding electronics can be optimized for the transmission of the fundamental frequency ultrasound pulses.

The signal lines 15a and 15b can be, in one example, constructed as coaxial cables running through the shaft 11 towards the tip 12. In one embodiment, further processing of the received signals can be performed as part of the reception circuitry 17b. Further ultrasound device specific circuitry can be applied to, for example, match the received signals with the ultrasound device to which they are fed.

As stated above, a limited space present inside the gastroscope probe also limits the kind of electronic circuitry being used. Preferably, the electronic circuitry is integrated into the tip 12 of the probe 10 and directly connected by specific means to the transducer elements 130b of the second, reception 2D-array 13b. The main purpose of the electronic circuitry is to further reduce the amount of reception signal lines or channels 15b leading from the 1000+ reception transducer elements 130b to a set of at least 64 to preferably no more than 256 reception signal lines 15b guided through the shaft 11 of the TEE probe 10.

In order to achieve this constructional reduction, several approaches can be followed:

a) Microbeam forming, i.e. the electronic combination of the signals of a subset of transducer elements of the 2D-array (subarray 20) by delay-and-sum circuitry into a single signal;

b) Isophase switching, i.e. the dynamic grouping of certain neighbouring elements in the array that should be assigned the same signal delays. These elements are switched in parallel by electronic switches for each received ultrasound channel;

c) Multiplexing in frequency of the received signals. Multiple band-limited signals are modulated to higher frequency bands and combined on a single coaxial cable or an optical fibre connection;

d) Multiplexing in time: multiple signals are sampled, possibly digitized and encoded, and their data combined to be transmitted as a single datastream in a single channel 15b.

The signal processing may be achieved either in the analog signal domain or after analog-to-digital conversion, by digital processing for part or even the whole of the signal processing chain.

The first and second 2D-arrays 13a-13b can have, depending on the intended use and functionality, identical or different sizes. In the latter embodiment, the dimensional size in longitudinal direction 10' of the first array 13a of transducer elements 130a is smaller than the dimensional size of the second 2D-array 13b of transducer elements 130b (see FIGS. 1-2).

Figure 3:
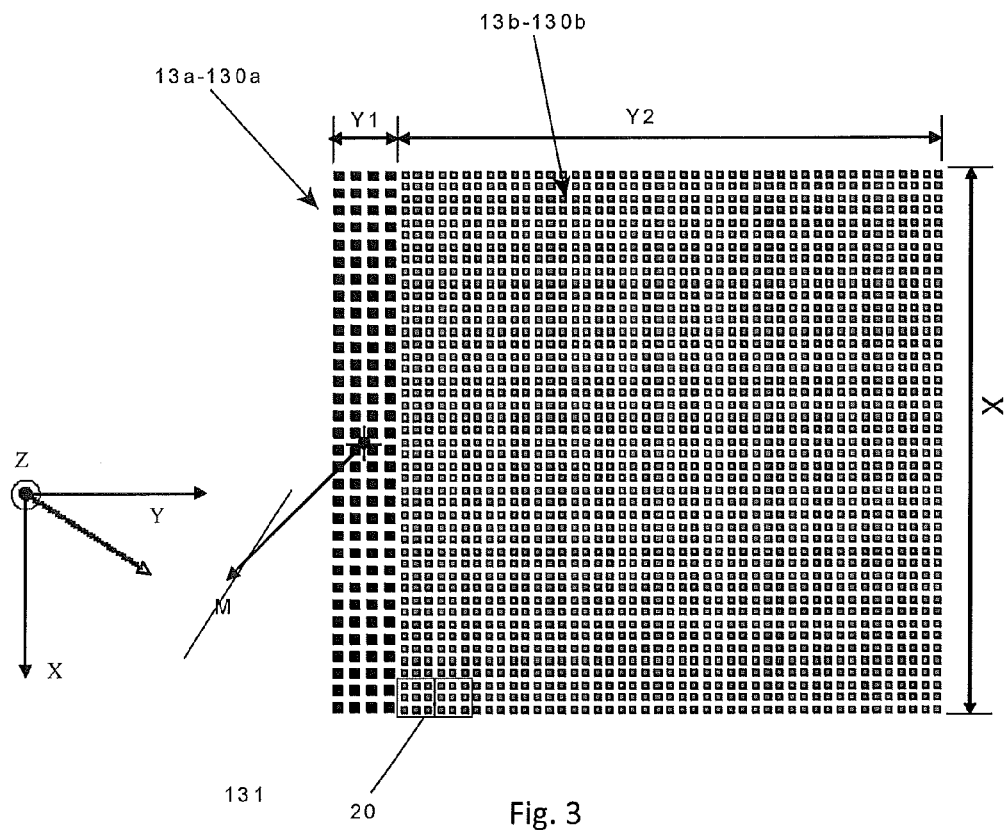
FIG. 3 illustrates a constructional overview of an ultrasound transducer comprising two 2D arrays of transducer elements.

Preferably, and as shown in FIGS. 1-3, the first 13a and second 13b array of transducer elements are arranged in a side-by-side manner in a longitudinal direction 10' of the probe tip 12.

In one embodiment, a further reduction is obtained when the arrays are connected as a sparse matrix, which is beneficial due to the constructional limitation of the head or tip 12 of the TEE probe 10, which can have a typical size of 30×15× 15 mm (length×width×height).

It should be clear that several configurations of the first and second arrays 13a-13b are possible in order to obtain a dual ultrasound transducer for use in an ultrasound imaging device according to the invention. The transducer elements 130a-130b in the arrays 13a-13b can have a rectangular, elliptic, triangular, or polygonal shape. The elements may be arranged in different types of two-dimensional grids, such as orthogonal, skewed, triangular, hexagonal or annular grids, as shown in FIGS. 4(a)-4(c). Also, different aperture shapes for both arrays are possible. The transducers elements 130a-130b can be manufactured from any suitable piezoelectric material or composite material.

Separating the transducer 13 in two physically separate transducer 2D-arrays 13a-13b enables improving the TEE probe. In particular, both the first and second 2D-arrays 130a-130b can be separately optimized in terms of aperture, transducer material and thickness, resonance frequency, element counts and element dimensions, matching layers and backing. This yields optimal transmission and reception characteristics of the two 2D-arrays of the dual transducer separately and independently. In this way, the probe can be made suitable for harmonic imaging, superharmonic imaging, subharmonic imaging, radial modulation etc.

Furthermore this separated array construction allows for a physical separation and shielding of the low-voltage reception and control electronics 17b-17b' and transmission signal lines 15b-15b from the high-voltage transmit signals 15a-15a, further reducing noise, interference etc., and alleviating the requirements for the reception circuitry 17b-17b.

The use of low-voltage integrated reception circuitry 17b' instead of high-voltage combined transmit/receive circuitry further reduces power consumption of electronic components.

As harmonic imaging, subharmonic or superharmonic imaging is possible with two narrowband arrays 13a-13b, no broadband array is needed. Since the transducer arrays 13a-13b can have a different element pitch and operating frequency, grating lobes can be suppressed. The first, transmitting transducer 13a can be fully optimized for transmitting the fundamental frequency in terms of aperture, transducer material, etc. The second, receiving transducer array 13b can be fully optimized in the same aspects for reception of the harmonic, subharmonic or superharmonic frequencies.

A frontal view of another embodiment of a transducer divided in two separated arrays 13a-13b is depicted in FIG. 3. A cartesian coordinate system is shown for further elucidation in the rest of the figurative description.

Dimension Y is the longitudinal direction of the shaft axis (reference numeral 10' in FIG. 1), dimension X is the width direction, dimension Z is the direction perpendicular to the probe surface. The center of the first, transmitting 2D-array 13a is defined as the origin of the dual transducer. Three dimensional angles are represented as azimuth and elevation. With azimuth it is meant the rotation angle in the X-Y plane, thus azimuth=0° coincides with the X-axis, whereas azimuth=90° coincides with the Y-axis. With elevation it is meant the angle relative to the X-Y plane, thus elevation=0°: the X- or Y-axis, elevation 901: the Z-axis.

In a preferred embodiment, the width X of the first, transmitting array 13a (seen in the X-direction) is 10 mm, while its length Y1 (in the Y-direction) is much smaller, and it has many elements in the X direction and few in the Y direction.

The first, transmitting 2D-array 13a has—in this embodiment demonstrated by way of an illustrative, non limiting example—a dimensional size of 10×1.25 mm (X×Y1) and consists of 32×4 transducer elements 130a with a pitch of 0.31 mm. The second, receiving 2D-array 13b has, in this embodiment, a dimensional size of 10×10 mm (X×Y2) and consists of 45×45 transducer elements 130b with a pitch of 0.2 mm. The remainder of the array (wafer die) can then be used for the bond pads that are distributed around the circumference thereof. The kerf 131 between the elements 130b is 30 μm. The kerf between the elements 130a can be the same or slightly larger. This configuration is designed for transmission at 3 MHz and reception at the second harmonic frequency (6 MHz).

In a second non limiting example, a more square type transmit array can be applied wherein for example 11×11 individual transducer elements 130b are comprised. This has the advantage that a higher amount of energy can be transmitted towards the target location.

The first, transmitting 2D-array 13a has in this embodiment a rectangular (non-square) aperture shape, whereas the second, receiving 2D-array 13b has a square or an almost square aperture shape. Also the first and second 2D-arrays 13a-13b are placed adjacent to each other.

In this embodiment, the second, receiving transducer 13b consisting of 2025 transducer elements 130b is divided into 15×15 subarrays 20 of 3×3 elements each. Each subarray 20 is producing one receiving signal by microbeamforming in the electronic circuitry 17b-17b' or, not depicted in FIGS. 1 and 2, at least partly in the transducer array stack 13b or attached reception electronics 14b. Thus, the 2025 transducer elements 130b are not each and individually connected to an output signal line (in coaxial cables 15b), but this signal line number is significantly reduced due to the creation of 225 subarrays 20 consisting of a subgroup of 9 transducer elements 130b.

Signal processing thus requires only 225 coaxial signal line cables resulting in a significant reduction in the number of signal lines 15b to be guided through the shaft 11. When 1:2 multiplexing is performed a further reduction can be achieved, if required, to 113 signal line cables.

The first, transmitting 2D-array 13a consists of 128 transducer elements 130a, which transducer elements can be directly connected via 128 coaxial cables 15a to the external mainframe. The transmitting and receiving cables 15a-15b can either be physically separated, or combined. However with this constructional approach a significant reduction can be achieved as together with power and control lines, the total number of signal cables can be less than 256.

In FIGS. 4a-4e, several alternative embodiments are shown depicting several possible element shapes and grid configurations for the 2D-arrays 13a or 13b. FIG. 4a depicts an orthogonal grid array having rectangular transducer elements 130, whereas FIG. 4b depicts a triagonal grid array having triangular transducer elements 130. A skewed grid pattern consisting of elliptic transducer elements 130 is shown in FIG. 4c and FIG. 4d shows a hexagonal grid array based on star-shaped elements. Finally in FIG. 4e an annular grid is shown.

Figure 5:
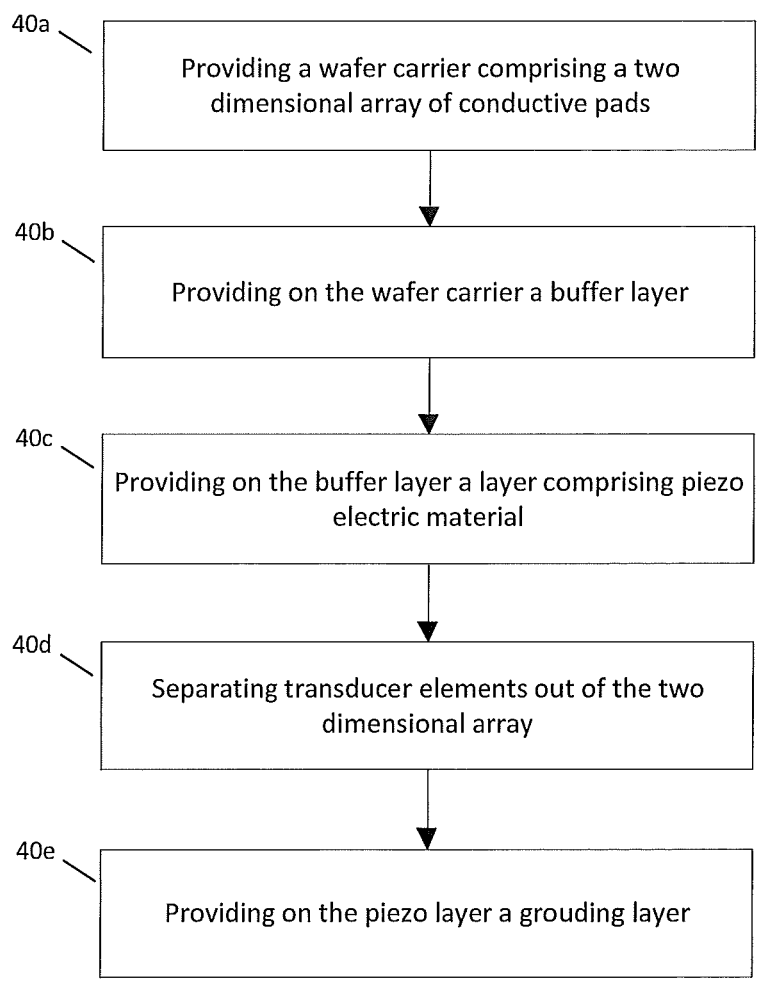
FIG. 5 illustrates a further example of the steps of manufacturing an ultrasound transducer for an ultrasound imaging device according to a further embodiment of the invention.

A method according to an aspect of the present invention is shown in FIG. 5, wherein an ultrasound transducer is manufactured with a (dual) 2D array of transducer elements. The method provides a high yield and high throughput for the manufacturing of high resolution ultrasound transducers wherein the transducer elements are formed by applying a layer of piezo electric material on a wafer carrier and subsequently dicing the individual elements out of the layer.

In the first step 40*a* of the method a wafer is provided. The wafer is a slice of semiconductor material used as a carrier on which a stack of layers is to be applied. The semiconductor material can be silicon or other known materials such as germanium, gallium, arsenide or silicon carbide, in pure form or including dopants such as boron or phosphorus.

The wafer carrier is manufactured with known semiconductor production methods. Microelectronic's can be formed in the layers of the wafer to drive the plurality of individual transducer elements, in the case of transducer elements arranged to transmit ultrasound. In the case of transducer elements arranged to receive ultrasound, as depicted in FIG. 1 with 13*b*, the transducer elements need to be connected for further processing outside the ultrasound probe 10. For example, as described above, micro-beam forming methods can be applied on the array of transducer elements to combine several individual transducer, elements in a subset of the 2D array by known delay-and-sum circuitry for further processing in a single signal over a single connection or wire.

Figure 4:
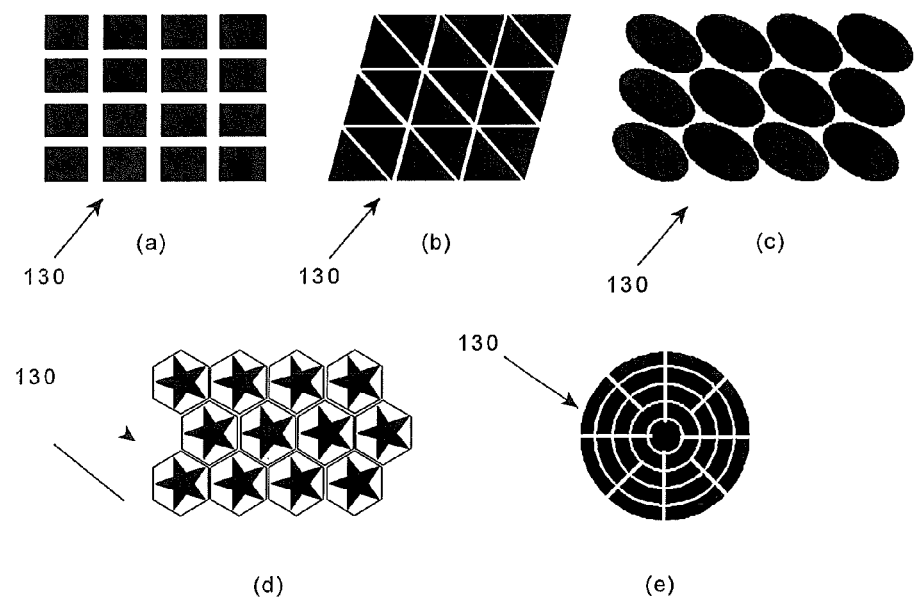
FIG. 4 illustrates examples of a two dimensional array of transducer elements.

Therefore, at least some of the electronic circuitry is provided in the wafer carrier to at least connect the individual ultrasound transducer elements. During manufacturing of the wafer carrier, a 2D array of conductive pads are created on a top face of the wafer carrier. The conductive pads are isolated from each other and can be provided in a variety of patterns and shapes such as those disclosed in FIG. 4. The most common shape is an orthogonal grid of individual conductive pads as shown in FIG. 4 (*a*).

Each individual conductive pads is electronically connected with an electronic circuit in a layer of the wafer carrier. These electronic circuits are in the most common form arranged as beam formers on chip. They are then addressable for further processing outside the wafer die, within the probe or even in the ultrasound transducer device. The electronic circuits can be addressed/connected at the top face of the wafer carrier via bond pads. From thereon, the circuits can be connected via bond wires or the like for further processing.

The beam former circuitry is, as described above, addressable via the conductive pads on the top face of the wafer carrier. They combine a large amount of individual electronic signals provided by/from the individual transducer elements. That way, the amount of wires can be reduced in the probe itself and a smaller amount of wires are needed for connecting the probe with the ultrasound device.

In the second step 40*b* of the method, a buffer layer is applied on the wafer carrier. The way in which this layer is applied goes beyond the scope of the invention and can be any suitable deposition or growing method. The buffer layer however requires certain specific properties. As the buffer layer forms part of the stack of layers on the wafer die from which the ultrasound transducer is produced, there are acoustic requirements. The buffer layer, when cut to a certain depth in a further step 40*d* of the method, forms a buffer in the vertical plane of the wafer die between the piezo layer and the carrier and in the horizontal plane of the wafer die between the individual piezo elements/transducer elements.

To prevent reflection and distortion of the transmitted ultrasound, the buffer layer is as acoustically transparent as possible. As the acoustic impedance is correlated to the material properties and the thickness of the layer, several combinations are possible. For example, if aluminium oxide is used as main compound of the buffer layer (or if the buffer layer only comprises aluminium oxide) the layer should have a thickness of around 15 to 25 μm for it to be acoustically transparent. However, reducing the thickness of the buffer layer reduces the tolerance for dicing at the step of separating the individual transducer elements 40*d* out of the piezo layer. Furthermore the buffer layer needs to have electrical isolating properties to prevent the individual piezo elements to short circuit.

In the next step, a layer of piezo electric material is provided 40*c* on top of the buffer layer. The method in which the layer is applied is also beyond the scope of the invention and can be similar to the methods described earlier. The piezo electric material can be a piezo ceramic comprising materials such as lead zirconate titanate or the like, or a crystal such as gallium orthophosphate or the like.

In step 40*d*, the stack is diced to form the individual transducer elements. The wafer carrier includes the conductive pads on the top face, on which the buffer layer is provided and on top thereof the piezo layer. Dicing can be performed by a number of methods, such as mechanical sawing or laser cutting. Most common dicing is by sawing with a diamond saw, during which the wafer is held steady on a frame and a saw cuts the wafer from the top face according to the pattern of the conductive pads, that being the 2D array. With the cuts, or streets, the piezo material is separated in a plurality of individual transducer elements arranged in the 2D array. The cuts have a width of 25 to 75 μm, and in particular they are 30 μm. The cuts are made to such a depth that all of the piezo material is cut. The cuts have a depth that reaches the buffer layer, thereby increasing the tolerance of the cutting by the thickness of the buffer layer.

For example, if the electronic circuitry in the wafer carrier is directly below the surface of the wafer and the stack further comprises a 25 μm thick buffer layer followed by a 250 μm thick layer of piezo material, during the cutting step the cuts can have a depth somewhere in the range between 250 and 275 μm. If the cut depth is set at 262.5 μm a cutting tolerance is allowed of 12.5 μm in both directions. If the buffer layer is provided with a layer thickness of 50 μm, the cutting tolerance is increased to 25 μm in both directions.

Finally, during step 40*e* the stack of layers is covered by a finalizing layer of electrical conductive material electrically connecting the top face of all the individual transducer elements and connecting them with ground. Herewith, the electrical circuits of the individual transducer elements are closed and the circuits are operable.

Figure 6:
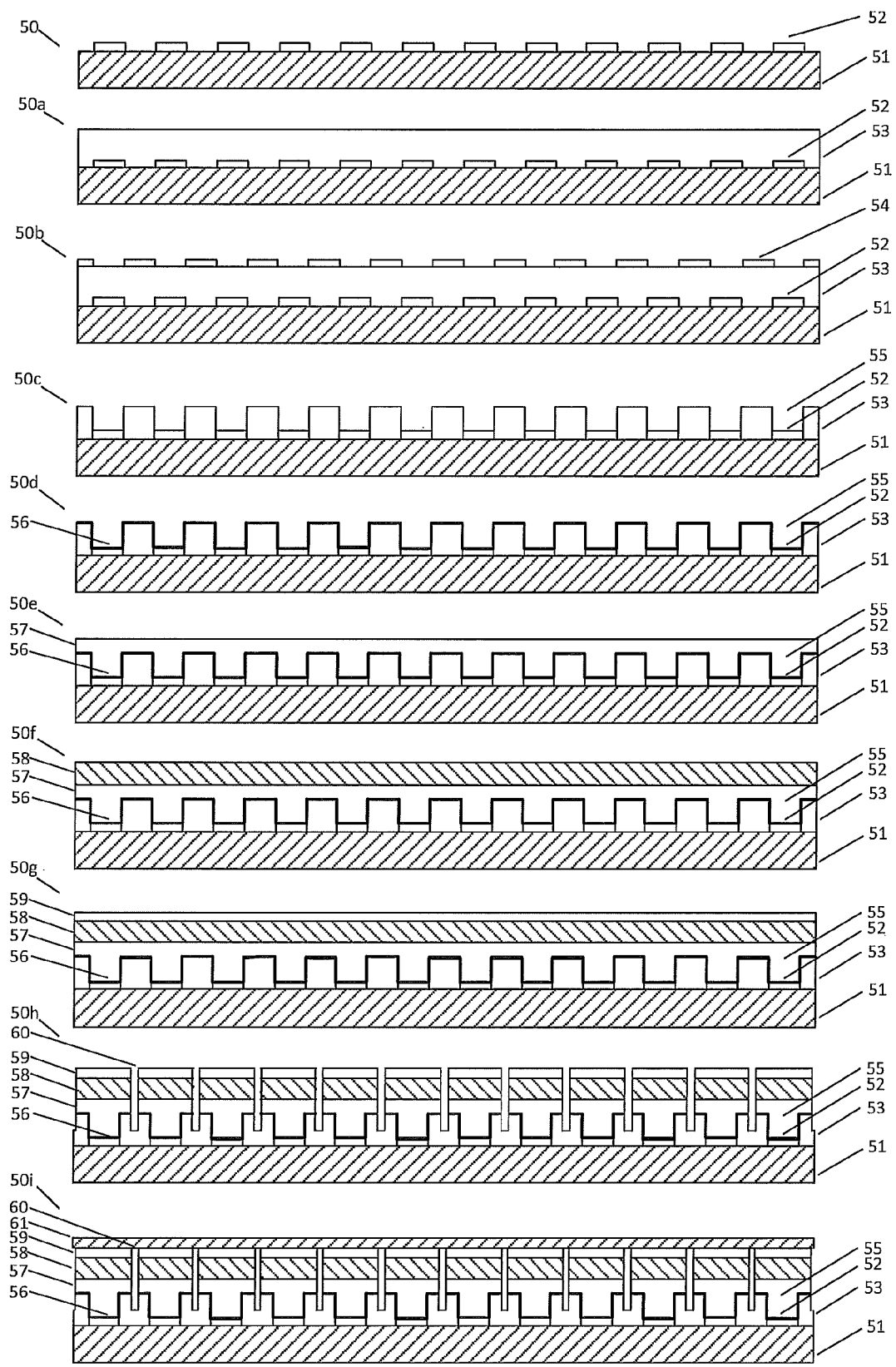
FIG. 6 illustrates an example of the steps of manufacturing an ultrasound transducer for an ultrasound imaging device according to an embodiment of the invention.

In FIG. 6, an example is disclosed for manufacturing an ultrasound transducer in an ultrasound probe of an ultrasound imaging device. The method comprises several steps 50-50*i*, during which steps layers are applied or material is removed on and from a wafer carrier. The wafer stack is diced during a separation step.

In step 50, a wafer is provided wherein at least some electronic circuitry is present in the wafer carrier. On top of the wafer carrier 51 plural conductive pads 52 are formed. These conductive pads 52 are arranged in a grid according to a 2D orthogonal array. However, in other embodiments, other grids can be used, such as the ones disclosed in the FIG. 4.

In the next step 50*a*, the wafer carrier is provided with a buffer layer including for example aluminium oxide or another electrical insulating material. Furthermore, the buffer layer material should be as acoustically transparent as possible so as not to influence the ultrasound waves transmitted and received by the individual transducer elements of the ultrasound transducers. If the angle of incidence is 0, the level of reflection of the ultrasound waves can be represented by the following equation:

$$R = \frac{(z_2 - z_1)}{(z_1 + z_2)}$$

The acoustic reflection of the ultrasound waves is a function of the acoustic impedance $z_1$ and $z_2$ of both materials. If the acoustic impedance of both materials is nearly the same, the reflection R according to the equation is minimal. As the acoustic impedance is the product of velocity and density, it is possible for two materials with different densities to have the same acoustic impedance. The acoustic reflection coefficient can have a value that ranges between −1 and +1.

Furthermore, for the buffer layer to be acoustically transparent, or at least have a high level of transparency, it needs to have a minimal thickness for the given material. For example, if a layer of aluminium is provided and acoustic signals are received at a second harmonic of 6 MHz, the layer needs to be much smaller than half a wavelength to prevent standing waves in a layer as the wavelength of the signals are that small that standing waves can appear at thicker layers. For other materials, other thicknesses apply, however they should also be thin enough to prevent standing waves.

During the next step 50b, a mask 54 is applied on the buffer layer for etching in the subsequent step 50c. The mask is applied corresponding to the grid in which the conductive pads 52 are arranged, for example in an orthogonal 2D array. Subsequently, the wafer stack with the buffer layer 53 on top is etched. At those positions on the buffer layer where no mask is applied, the entire layer is removed. At least a part of the layer, or depending on the etching time and rate, the whole of the layer can be removed. With a highly selective etch, the buffer layer can be removed without removing the underlying wafer layer. In one embodiment, isotropic instead of anisotropic etches can be applied to produce round side walls instead of vertical ones.

After etching, the stack includes buckets 55 with a depth to the wafer carrier. The conductive paths are exposed at the bottom of these buckets. Good electrical connection between the piezo material and the conductive pads is thus realized. To increase the contact area of the conductive pad, in step 50d an additional layer 56 is provided in/over the buckets. This additional layer 56 includes electrically conductive material, such as aluminium, to increase the electrical contact of the conductive pads 52. This layer is advantageously applied in a thin layer. It can be either grown or provided on top of the stack in the form of a glue or glue-like material.

Next, in step 50e, a fluidic material 57 is provided on the wafer stack. This material 57 is fluidic such that it flows and fills the buckets 55 formed in the buffer layer 53. This fluidic material, or glue 57, is electrically conductive so as to make an electric connection possible between the top of the glue 57, via the additional electrical conductive layer 56 and the conductive pads 52 to the electronic circuitry below the surface of the wafer carrier 51. After application the glue adheres with the conductive layer 56 below. In one embodiment, the glue 57 is applied in such a layer and has an acoustic impedance, and thickness that matches the adjacent layers. The glue can be a fine grain electrically conductive glue to make sure the buckets are fully filled to make electrical contact with the conductive pads and to minimize the amount of air in the buckets as this has a negative effect on the acoustic properties of the stack.

During step 50f, the piezo electric material is applied on the stack. This can either be a (single) crystal such as gallium orthophosphate ($GaPO_4$) or quartz, Langasite ($LA_3Ga_5SiO_{14}$) or the like, or in an advantageous example a ceramic material such as lead titanate ($PbTiO_3$) or lead zirconate titanate (PZT) or the like. The piezo material can have golden electrodes to ensure connection with the adjacent layers. If PZT is used as a piezo ceramic layer, the acoustic impedance is around 38 MRayls.

As the acoustic impedance of the piezo ceramic is relatively high, the ultrasound waves would to a certain degree be reflected at the interface of the medium. To minimize this effect, in step 50g an additional layer 59 is applied, which layer is electrically conductive, and is used as an acoustic matching layer for the outside environment of the probe and the piezo material. Air has an acoustic impedance of around 500 Rayl and human tissue lies between 1.4 MRayl and 1.7 MRayl (except for bone which is much higher). When an additional layer 59 is applied on the stack this layer can be used to acoustically match the layer of piezo material with the outside and measured tissue, organ, arteries, etc. For example, a layer having an acoustic impedance of 7 MRayl can match the adjacent layer of the piezo and the outside.

After applying these layers, the stack can be diced in a dicing step 50h. Upon dicing, the whole stack, except the wafer carrier itself, is cut according to the same grid as the remaining material in the buffer layer. In between the individual conductive pads, streets 60 are formed with a width in the range between 25 μm and 75 μm, more in particular between 25 and 50 μm, and more specific 30 μm. The depth of the cuts/streets 60 is at least up until the buffer layer 57, but in practice around 10 μm deep inside the buffer layer 57 if the buffer layer is for example applied with a 25μ layer thickness. Upon dicing the individual piezo elements are formed as there are cut according to a 2D grid. Plural individual stacks are created, which form the individual transducer elements. As there is no electrical or even physical contact (due to air in the streets) between the individual transducer elements, they can be operated individually by the electric circuitry below the wafer carrier surface and connected by the conductive pads.

To close the electric circuits, the top side of the stack of individual transducer elements is provided in step 50i with a layer of electric conductive material 61, which layer is then grounded. Besides the individual circuits by grounding them, this layer further functions to stabilize the individual stacks. By applying a grounding layer 61, the individual transducer elements are locked between the wafer carrier and the grounding layer, increasing the stability of the whole transducer unit.

From the detailed description above, it is apparent that variations are possible. Different choices of materials having the required acoustic properties and dimensions are also possible. Hence, the above described invention has been shown and described with reference to example embodiments, a person skilled in the art will understand that other choices of materials and dimensions are merely details that fall within the scope and in particular the claims of the invention.

What is claimed is:

1. A method of manufacturing an ultrasound transducer for an ultrasound imaging device including a plurality of transducer elements arranged in a two dimensional array on a single carrier of semi-conductor material, the ultrasound transducer including a stack of lack of layers, the method comprising the steps of:
   providing a carrier of semi-conductor material including a two dimensional array of conductive pads, wherein the carrier of semi-conductor material includes electronic circuitry connected with the conductive pads for further processing outside the ultrasound transducer;

providing on the carrier a layer including piezo electrical material covering the two dimensional array of conductive pads;

separating each of the plurality of transducer elements by dicing the two dimensional array on the carrier; and providing a grounding layer on the plurality of transducer elements for grounding each transducer element; and providing a buffer layer between the carrier and the layer comprising the piezo electrical material, wherein said dicing is performed with cuts having a depth that reaches the buffer layer, and wherein the method further comprises the steps of:

applying a mask on the buffer layer in a pattern corresponding with the two dimensional array of conductive pads; and etching the buffer layer, whereby buckets are formed corresponding with the pattern including the conductive pads.

2. The method according to claim 1, further comprising the step of:

providing a layer including electrically conductive material on the buffer layer for electrically connecting the layer of piezo electrical material with the conductive pads in the buckets of the carrier.

3. The method according to claim 1, further comprising the step of:

providing a layer including electrically conductive material for filling the buckets including the conductive pads.

4. The method according to claim 2, wherein the layer of electrically conductive material includes acoustical properties arranged for acoustically matching the carrier with the layer of piezo electrical material.

5. The method according to claim 1, further comprising the step of:

providing a layer including electrically conductive material on the buffer layer, connected with the conductive pads in the bucket.

6. The method according to claim 1, further comprising the step of:

providing a layer including electrically conductive material between the layer of piezo electrical material and the grounding layer.

7. The method according to claim 6, wherein the layer including the electrically conductive material has acoustical properties for acoustically matching the layer of piezo electrical material with the outside environment.

8. The method according to claim 1, wherein the buffer layer is a layer including electrical isolating material.

9. The method according to claim 1, wherein the buffer layer is a layer including acoustically transparent properties.

10. The method according to claim 1, wherein the buffer layer includes an aluminum oxide.

11. The method according to claim 1, wherein the step of separating each of the plurality of transducer elements includes scribing, breaking, sawing or laser cutting the two dimensional array on the carrier.

12. The method according to claim 1, wherein the electronic circuitry in the carrier is arranged for electronically aggregating plural transducer elements for further processing outside the ultrasound transducer.

* * * * *